United States Patent
Groth

(10) Patent No.: US 11,896,660 B1
(45) Date of Patent: *Feb. 13, 2024

(54) REDUCING HOSPITALIZATION IN ELDERLY INFLUENZA VACCINE RECIPIENTS

(71) Applicant: Seqirus UK Limited, Berkshire (GB)

(72) Inventor: Nicola Groth, Siena (IT)

(73) Assignee: Seqirus UK Limited, Berkshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/788,044

(22) Filed: Oct. 19, 2017

Related U.S. Application Data

(63) Continuation of application No. 13/279,156, filed on Oct. 21, 2011, now Pat. No. 9,821,051.

(60) Provisional application No. 61/573,492, filed on Sep. 6, 2011, provisional application No. 61/456,035, filed on Oct. 28, 2010.

(51) Int. Cl.
  *A61K 39/145* (2006.01)
  *A61K 47/00* (2006.01)

(52) U.S. Cl.
  CPC ............ *A61K 39/145* (2013.01); *A61K 47/00* (2013.01)

(58) Field of Classification Search
  None
  See application file for complete search history.

(56) References Cited

U.S. PATENT DOCUMENTS

| | | |
|---|---|---|
| 5,162,112 A | 11/1992 | Oxford et al. |
| 6,838,089 B1 | 1/2005 | Carlsson et al. |
| 6,869,607 B1 | 3/2005 | Buschle et al. |
| 2005/0186621 A1 | 8/2005 | Galarza et al. |
| 2006/0211644 A1 | 9/2006 | Krieg et al. |
| 2007/0141078 A1 | 6/2007 | D'Hondt et al. |
| 2009/0220541 A1 | 9/2009 | O'Hagan |
| 2009/0263422 A1 | 10/2009 | Hanon et al. |
| 2011/0014230 A1 | 1/2011 | Haussmann et al. |
| 2012/0027813 A1 | 2/2012 | Podda et al. |
| 2012/0064117 A1 | 3/2012 | Ross et al. |
| 2012/0093860 A1 | 4/2012 | Stohr et al. |

FOREIGN PATENT DOCUMENTS

| | | |
|---|---|---|
| WO | WO 2005/113756 | 12/2005 |
| WO | WO 2006/098901 | 9/2006 |
| WO | WO 2006/100110 | 9/2006 |
| WO | WO 2007/052057 | 5/2007 |
| WO | WO 2007/052058 | 5/2007 |
| WO | WO 2007/052059 | 5/2007 |
| WO | WO 2007/052061 | 5/2007 |
| WO | WO 2007/052155 | 5/2007 |
| WO | WO 2007/110776 | 10/2007 |
| WO | WO 2008/032219 | 3/2008 |
| WO | WO 2008/068631 | 6/2008 |

OTHER PUBLICATIONS

Kumar et al., "Influenza Vaccination in Renal Transplant Recipients," JAMA 239:840-842 (Year: 1978).*
Lanternier et al., "Factors influencing influenza vaccination in adults under immunosuppressive therapy for a systemic inflammatory disease," Medecine et maladies infectieuses 39:247-251 (Year: 2009).*
Bellei et al., "Risk Factors for Poor Immune Response to Influenza Vaccination in Elderly People," The Brazilian Journal of Infectious Diseases 10(40: 269-273 (Year: 2006).*
"Abstracts of the 43rd Annual Meeting society for Epidemiologic Research Anaheim, California, Jun. 23-26, 2010," Am. J. Epidemiol. (2010) 171 (suppl 11): S1-S157.
Australian Department of Health website displaying Barr et al., "Circulation and antigenic drift in human influenza B viruses in SE Asia and Oceania since 2000," Commun Dis Intell. 30(3):350-357, (2006), Web page updated as of Sep. 30, 2006, 17 pages.
Baldo et al., "Response to influenza vaccine in people with non-protective HI antibody titers," Eur J Epidemiol, 21(11):843-845, (2006).
Banzhoff et al., "MF59-adjuvanted vaccines for seasonal and pandemic influenza prophylaxis," Influenza Other Respir Viruses, 2(6):243-249, (2008).
Barr et al., "Circulation and antigenic drift in human influenza B viruses in SE Asia and Oceania since 2000," Commun Dis Intell.,30(3):350-357, Abstract only, (2000).
Barr et al., "Reassortants in recent human influenza A and B isolates from South East Asia and Oceania," Virus Res, 98(1):35-44, (2003).
Beran et al., "Immunogenicity and safety of quadrivalent versus trivalent inactivated influenza vaccine: a randomized, controlled trial in adults," BMC Infect Dis, 13:224, (2013).
Chan et al., "Phylogenetic analysis of influenza B virus in Taiwan, 1997 to 2001," J Microbial Immunol Infect., 37(3):135-144, (2004).
Dapat et al., "Genetic characterization of human influenza viruses in the pandemic (2009-2010) and post-pandemic (2010-2011) periods in Japan," PLoS One, 7(6):e36455, (2012).
Della Cioppa et al., "Trivalent and quadrivalent MF59(®)-adjuvanted influenza vaccine in young children: a dose- and schedule-finding study," Vaccine, 29(47):8696-8704, (2011).
De Donato et al., "Safety and immunogenicity of MF59-adjuvanted influenza vaccines in the elderly," Vaccine, 17(23-24):3094-3101, (1999).
Duggan et al., "Intanza 15 microg intradermal seasonal influenza vaccine: in older adults (aged >or=60 years)," Drugs Aging, 27(7):597-605, (2010).

(Continued)

*Primary Examiner* — M Franco G Salvoza
(74) *Attorney, Agent, or Firm* — Finnegan, Henderson, Farabow, Garrett & Dunner, LLP

(57) ABSTRACT

Compared to an unadjuvanted vaccine, an adjuvanted influenza vaccine can reduce by almost a quarter the risk of hospitalization for respiratory illness (e.g. influenza and pneumonia) in elderly recipients. Thus the invention provides a method for immunizing an elderly subject by administering an adjuvanted influenza vaccine, whereby the subject's risk of hospitalization for respiratory illness (e.g. influenza and pneumonia) is reduced relative to an elderly subject who receives an unadjuvanted influenza vaccine.

21 Claims, No Drawings

(56) References Cited

OTHER PUBLICATIONS

Durando et al., "MF59-adjuvanted vaccine: a safe and useful tool to enhance and broaden protection against seasonal influenza viruses in subjects at risk," Expert Opin Biol Ther, 10(4):639-651, (2010).
Eickhoff, "The 2005 to 2006 influenza season is over," Infectious Disease News, 3 pages, (2006).
Elliot et al., "Influenza and respiratory syncytial virus in the elderly," Expert Rev Vaccines, 7(2):249-258, (2008).
FDA News Release, "FDA approves first quadrivalent vaccine to prevent seasonal influenza," 2 pages, (2012).
Govaert et al., "Immune response to influenza vaccination of elderly people. A randomized double-blind placebo-controlled trial," Vaccine, 12(13):1185-1189, (1994).
Govaert et al., "The efficacy of influenza vaccination in elderly individuals. A randomized double-blind placebo-controlled trial," JAMA, 272(21):1661-1665, (1994).
Gasparini et al., "Increased immunogenicity of the MF59-adjuvanted influenza vaccine compared to a conventional subunit vaccine in elderly subjects," Eur J Epidemiol, 17(2):135-140, (2001).
Higgins et al., "MF59 adjuvant enhances the immunogenicity of influenza vaccine in both young and old mice," Vaccine, 14(6):478-484, (1996).
Hiromoto et al., "Phylogenetic analysis of the three polymerase genes (PB1, PB2 and PA) of influenza B virus," J Gen Virol, 81(Pt 4):929-937, (2000).
Jackson et al., "Influenza vaccination and risk of community-acquired pneumonia in immunocompetent elderly people: a population-based, nested case-control study," Lancet, 372(9636):398-405, (2008).
Jefferson et al., "Vaccines for preventing influenza in the elderly," Cochrane Database Syst Rev. 17(2):CD004876, (2010).
Kashiwagi, "Measures against influenza. Influenza and vaccine," JIM, 9(11):971-974, (1999).
Kishida et al., "Evaluation of influenza virus A/H3N2 and B vaccines on the basis of cross-reactivity of postvaccination human serum antibodies against influenza viruses A/H3N2 and B isolated in MDCK cells and embryonated hen eggs," Clin Vaccine Immunol, 19(6): 897-908, (2012).
Kurashige et al., "Prevention of influenza by vaccination," Sago Rinsho (General Clinical), 49(2):285-288, (2000).
Levandowski et al., "Antibody responses to influenza B viruses in immunologically unprimed children," Pediatrics, 88(5):1031-1036, (1991).
Lin et al., "Recent changes among human influenza viruses," Virus Res, 103(1-2):47-52, (2004).
MedImmune, "MedImmune Announces FDA Approval of First Four-strain Flu Vaccine, Flu Mist® Quadrivalent (Influenza Vaccine Live, Intranasal)," 3 pages, (2012).
Meijer et al., "Euroroundup: Epidemiological and virological assessment of influenza activity in Europe, during the 2004-2005 winter," Eurosurveillance, vol. 11, Issue 5, 16 pages, (2006).
Meydani et al., "Vitamin E supplementation enhances cell-mediated immunity in healthy elderly subjects," Am J Clin Nutr, 52(3):557-563, (1990).
Minutello et al., "Safety and immunogenicity of an inactivated subunit influenza virus vaccine combined with MF59 adjuvant emulsion in elderly subjects, immunized for three consecutive influenza seasons," Vaccine, 17(2):99-104, (1999).
Morio et al., "Three year follow up study of national influenza vaccination practices in Japan," J Epidemiol Community Health, 48(1):46-51, (1994).
Odagiri, "Methods to select influenza vaccine strain and problems in vaccine, future perspective for improvement," Shoni-Ka (Paediatric Service), 53(10):1355-1365, (2012).

O'Hagan, "MF59 is a safe and potent vaccine adjuvant that enhances protection against influenza virus infection," Expert Rev Vaccines, 6(5):699-710, (2007).
Ott et al., "Enhancement of humoral response against human influenza vaccine with the simple submicron oil/water emulsion adjuvant MF59," Vaccine, 13(16):1557-1562, (1995).
Plotkin and Orenstein. *Vaccines*, 4th Edition, p. 349, (2003).
Puig-Barberà et al., "Effectiveness of MF59-adjuvanted subunit influenza vaccine in preventing hospitalisations for cardiovascular disease, cerebrovascular disease and pneumonia in the elderly," Vaccine, 25(42):7313-7321, (2007).
Remarque et al., "Altered antibody response to influenza H1N1 vaccine in healthy elderly people as determined by HI, ELISA, and neutralization assay," J Med Virol, 55(1):82-87, (1998).
Saito et al., "Antigenic alteration of influenza B virus associated with loss of a glycosylation site due to host-cell adaptation," J Med Virol, 74(2):336-343, (2004).
Sakoh, "Antibody response of influenza vaccine and laboratory examination of prevaccination in the aged," Kurume-Igakukaizassi (Journal of KURUME Association of Medical Science), 52(11):1157-1167, (1989).
Schneider et al., "Antibody response to tetravalent influenza subunit vaccine in patients infected with human immunodeficiency virus type 1," Int J Antimicrob Agents, 6(4):195-200, (1996).
Squarcione et al., "Comparison of the reactogenicity and immunogenicity of a split and subunit-adjuvanted influenza vaccine in elderly subjects," Vaccine, 21(11-12):1268-1274, (2003).
Stephenson et al., "Cross-reactivity to highly pathogenic avian influenza H5N1 viruses after vaccination with nonadjuvanted and MF59-adjuvanted influenza A/Duck/Singapore/97 (H5N3) vaccine: a potential priming strategy," J Infect Dis, 191(8):1210-1215, (2005).
Tada, "Novel A(H1N1) Inactivated Influenza Split Vaccine," Rinsho-to-uirusu (Clinical and Virus), 38(1):62-75, (2010).
Tada, "Influenza Vaccine," Rinsho-to-biseibutsu (Clinical and Microorganism), 37:053-060, (2010).
Tsai et al., "Increasing appearance of reassortant influenza B virus in Taiwan from 2002 to 2005," J Clin Microbiol, 44(8):2705-2713, (2006).
VRBPAC Teleconference Mar. 6, 2002 Preliminary Summary, 1 page. Available at <http://www.fda.qov/ohrms/DOCKETS/ac/02/minutes/3842m1 preliminary 2.htm>.
WHO, "Recommended composition of influenza virus vaccines for use in the 1991-1992 season," 66(9):57-64, (1991).
WHO, "Recommended composition of influenza virus vaccines for use in the 2006-2007 influenza season," retrieved online, 5 pages, (2006).
WHO, "Recommended composition of influenza virus vaccines for use in the 2012-2013 northern hemisphere influenza season," 16 pages, (2012).
WHO, "Recommended composition of influenza virus vaccines for use in the 2013-2014 northern hemisphere influenza season," 21 pages, (2013).
WHO, "Recommended composition of influenza virus vaccines for use in the 2014-2015 northern hemisphere influenza season." 15 pages, (2014).
WHO Questions and Answers, "Recommended composition of influenza virus vaccines for use in the northern hemisphere 2014-15 influenza season and development of candidate vaccine viruses for pandemic preparedness," 4 pages, (2014).
Wood, "Selection of influenza vaccine strains and developing pandemic vaccines," Vaccine, 20(Suppl 5):B40-B44, (2002).
Xu et al., "Multiple lineages co-circulation and genetic reassortment of the neuraminidase and hemagglutinin genes within influenza viruses of the same type/subtype," International Congress Series 1219:383-387, (2001).

\* cited by examiner

REDUCING HOSPITALIZATION IN ELDERLY INFLUENZA VACCINE RECIPIENTS

This application is a continuation of U.S. application Ser. No. 13/279,156, filed Oct. 21, 2011, now U.S. Pat. No. 9,821,051, which claims the benefit of U.S. provisional applications 61/456,035 (filed Oct. 28, 2010) and 61/573,492 (filed Sep. 6, 2011), the complete contents of each of which are hereby incorporated herein by reference for all purposes.

TECHNICAL FIELD

This invention is in the field of immunization against influenza.

BACKGROUND ART

Active immunisation against influenza virus has been performed for many years. As of 2010 this involves seasonal production of trivalent vaccines which are then administered to at-risk populations, usually before winter begins. Current vaccines are mainly based on inactivated viruses, with dosing being based on their amount of viral hemagglutinin, but there is also one live attenuated vaccine.

In addition to seasonal trivalent vaccines the 2009 "swine flu" H1N1 pandemic led to widespread use of a monovalent vaccine.

All but one of the current seasonal vaccines licensed in the developed world are unadjuvanted. The exception is the FLUAD™ product which is adjuvanted with a squalene-in-water emulsion called MF59™. Oil-in-water emulsion adjuvants were also included in several monovalent H1N1 pandemic vaccines such as FOCETRIA™ and CELTURA™ (both with MF59™ adjuvant), AREPANRIX and PANDEMRIX (both with AS03 adjuvant), and HUMENZA (with AF03 adjuvant). The aim of including adjuvants in these vaccines is to improve the immune response which is mounted against the viral antigens.

Inclusion of an adjuvant can increase the quality and/or quantity of a recipient's immune response against influenza vaccines. A large number of clinical trials with MF59™-adjuvanted influenza vaccines have confirmed that the adjuvant provides higher immunogenicity and also protects better against infection with heterovariant potentially mismatched strains [1], but these effects have not been shown in epidemiological studies to avert cases of influenza or to reduce related complications.

SUMMARY OF THE INVENTION

Reference 2 reports that conventional influenza vaccines are modestly effective in preventing hospitalization and mortality of the elderly during the influenza season. The inventors have now found that, in comparison to a conventional unadjuvanted influenza vaccine, an adjuvanted influenza vaccine can reduce by almost a quarter the risk of hospitalization for respiratory illness (e.g. for influenza and pneumonia) in elderly recipients. Thus the invention provides a method for immunizing an elderly subject by administering an adjuvanted influenza vaccine, whereby the subject's risk of hospitalization for respiratory illness (e.g. for influenza and/or pneumonia) is reduced relative to an elderly subject who receives an unadjuvanted influenza vaccine.

The Elderly Subject

The invention concerns the immunisation of elderly subjects. The subject is a male or female human who is at least 65 years old e.g. between 65-100 years old, between 65-95 years old, between 65-90 years old, between 65-85 years old, between 65-80 years old, between 65-75 years old, etc. Thus the vaccine may be indicated for active immunization of persons 65 years of age and older against influenza disease e.g. influenza disease caused by influenza virus subtypes A and type B.

The elderly subject is preferably a community-dwelling elderly subject. In these embodiments the subject would not be resident in a hospital, a nursing home, or a rehabilitation center. Moreover, the subject would ideally not have been resident in a hospital, nursing home, or rehabilitation center in the 30 days preceding their receipt of the adjuvanted influenza vaccine.

If the vaccine is prepared from viruses which were grown in eggs then the elderly subject is preferably not hypersensitive to egg proteins.

The elderly subject is preferably not a person who previously received an influenza vaccine and exhibited a life-threatening reaction thereto.

In some embodiments the elderly subject is immunocompromised or is receiving immunosuppressive therapy.

In some embodiments the elderly subject is has taken an antiviral compound (e.g. an oseltamivir or zanamivir compound) in the 7 days prior to receiving the vaccine.

The Influenza Vaccine

The invention involves administering an adjuvanted influenza vaccine to an elderly subject. The influenza vaccine can take various forms e.g. as disclosed in chapters 17 & 18 of reference 3.

Current influenza vaccines are based either on inactivated or live attenuated viruses. Inactivated vaccines (whole virus, split virion, or surface antigen) are administered by intramuscular or intradermal injection, whereas live vaccines are administered intranasally. The invention can use with all of these vaccine forms, but preferably uses an inactivated vaccine, such as a split virus antigen vaccine or a purified surface antigen vaccine. The inactivated vaccine is preferably administered intramuscularly.

Some embodiments of the invention use a surface antigen influenza vaccine (inactivated). Such vaccines contain fewer viral components than a split or whole virion vaccine. They include the surface antigens hemagglutinin and, typically, also neuraminidase. Processes for preparing these proteins in purified form from influenza viruses are well known in the art. The FLUVIRIN™ AGRIPPAL™ and INFLUVAC™ products are examples of surface antigen influenza vaccines.

Other embodiments of the invention can use whole virus, split virus, virosomes, live attenuated virus, or recombinant hemagglutinin. These vaccines can easily be distinguished from surface antigen vaccines by testing their antigens e.g. for the presence of extra influenza virus proteins.

Whole inactivated virus can be obtained by harvesting virions from virus-containing fluids (e.g. obtained from eggs or from culture medium) and then treating them as described above.

Split virions are obtained by treating purified virions with detergents (e.g. ethyl ether, polysorbate 80, deoxycholate, tri-N-butyl phosphate, Triton X-100, Triton N101, cetyltrimethylammonium bromide, Tergitol NP9, etc.) to produce subvirion preparations, including the 'Tween-ether' splitting process. Methods of splitting influenza viruses, for example are well known in the art e.g. see refs. 4-9, etc. Splitting of the virus is typically carried out by disrupting or fragmenting whole virus, whether infectious or non-infectious with a disrupting concentration of a splitting agent. The disruption results in a full or partial solubilisation of the virus proteins, altering the integrity of the virus. Preferred splitting agents are non-ionic and ionic (e.g. cationic) surfactants e.g. alkylglycosides, alkylthioglycosides, acyl sugars, sulphobetaines, betains, polyoxyethylene-alkylethers, N,N-dialkyl-Glucamides, Hecameg, alkylphenoxy-polyethoxyethanols, NP9, quaternary ammonium compounds, sarcosyl, CTABs (cetyl trimethyl ammonium bromides), tri-N-butyl phosphate, myristyltrimethylammonium salts, lipofectin, lipofectamine, and DOT-MA, the octyl- or nonylphenoxy polyoxyethanols (e.g. the Triton surfactants, such as Triton X-100 or Triton N101), polyoxyethylene sorbitan esters (the Tween surfactants), polyoxyethylene ethers, polyoxyethlene esters, etc. One useful splitting procedure uses the consecutive effects of sodium deoxycholate and formaldehyde, and splitting can take place during initial virion purification (e.g. in a sucrose density gradient solution). Thus a splitting process can involve clarification of the virion-containing material (to remove non-virion material), concentration of the harvested virions (e.g. using an adsorption method, such as $CaHPO_4$ adsorption), separation of whole virions from non-virion material, splitting of virions using a splitting agent in a density gradient centrifugation step (e.g. using a sucrose gradient that contains a splitting agent such as sodium deoxycholate), and then filtration (e.g. ultrafiltration) to remove undesired materials. Split virions can usefully be resuspended in sodium phosphate-buffered isotonic sodium chloride solution. Examples of split vaccines are the BEGRIVAC™, INTANZA™, FLUARIX™, FLUZONE™ and FLUSHIELD™ products.

Virosomes are nucleic acid free viral-like liposomal particles [10]. They can be prepared by solubilization of virus with a detergent followed by removal of the nucleocapsid and reconstitution of the membrane containing the viral glycoproteins. An alternative method for preparing virosomes involves adding viral membrane glycoproteins to excess amounts of phospholipids, to give liposomes with viral proteins in their membrane.

Live attenuated viruses are obtained from viruses (grown in eggs or in cell culture), but the viruses are not inactivated. Rather, the virus is attenuated ("att") e.g. so as not to produce influenza-like illness in a ferret model of human influenza infection. It may also be a cold-adapted ("ca") strain i.e. it can replicate efficiently at 25° C., a temperature that is restrictive for replication of many wildtype influenza viruses. It may also be temperature-sensitive ("ts") i.e. its replication is restricted at temperatures at which many wild-type influenza viruses grow efficiently (37-39° C.). The cumulative effect of the ca, ts, and att phenotype is that the virus in the attenuated vaccine can replicate in the nasopharynx to induce protective immunity in a typical human subject, but it does not cause disease i.e. it is safe for general administration to the target human population. These viruses can be prepared by purifying virions from virion-containing fluids e.g. after clarification of the fluids by centrifugation, then stabilization with buffer (e.g. containing sucrose, potassium phosphate, and monosodium glutamate). Live vaccines include the FLUMIST™ product. Although live vaccines can be used with the invention, it is preferred to use non-live vaccines.

As an alternative to using antigens obtained from virions, haemagglutinin can be expressed in a recombinant host (e.g. in an insect cell line, such as Sf9, using a baculovirus vector) and used in purified form [11-13] or in the form of virus-like particles (VLPs; e.g. see references 14 & 15).

Where the vaccine includes antigens obtained from virions, these virions may have been produced by viral growth in eggs or in cell culture (see below). The current standard method for influenza virus growth for vaccines uses embryonated SPF hen eggs, with virus being purified from the egg contents (allantoic fluid). If egg-based viral growth is used then one or more amino acids may be introduced into the allantoid fluid of the egg together with the virus [9]. Virus is first grown in eggs. It is then harvested from the infected eggs. Virions can be harvested from the allantoic fluid by various methods. For example, a purification process may involve zonal centrifugation using a linear sucrose gradient solution that includes detergent to disrupt the virions. Antigens may then be purified, after optional dilution, by diafiltration. Chemical means for inactivating a virus include treatment with an effective amount of one or more of the following agents: detergents, formaldehyde, β-propiolactone, methylene blue, psoralen, carboxyfullerene (C60), binary ethylamine, acetyl ethyleneimine, or combinations thereof. Non-chemical methods of viral inactivation are known in the art, such as for example UV light or gamma irradiation.

Some embodiments of the invention use influenza vaccine prepared from viruses which were grown in cell culture, rather than in eggs. When cell culture is used, the viral growth substrate will typically be a cell line of mammalian origin. Suitable mammalian cells of origin include, but are not limited to, hamster, cattle, primate (including humans and monkeys) and dog cells. Various cell types may be used, such as kidney cells, fibroblasts, retinal cells, lung cells, etc. Examples of suitable hamster cells are the cell lines having the names BHK21 or HKCC. Suitable monkey cells are e.g. African green monkey cells, such as kidney cells as in the Vero cell line. Suitable dog cells are e.g. kidney cells, as in the MDCK cell line. Thus suitable cell lines include, but are not limited to: MDCK; CHO; 293T; BHK; Vero; MRC-5; PER.C6; WI-38; etc. Preferred mammalian cell lines for growing influenza viruses include: MDCK cells [16-19], derived from Madill Darby canine kidney; Vero cells [20-22], derived from African green monkey (*Cercopithecus aethiops*) kidney; or PER.C6 cells [23], derived from human embryonic retinoblasts. These cell lines are widely available e.g. from the American Type Cell Culture (ATCC) collection, from the Coriell Cell Repositories, or from the European Collection of Cell Cultures (ECACC). For example, the ATCC supplies various different Vero cells under catalog numbers CCL-81, CCL-81.2, CRL-1586 and CRL-1587, and it supplies MDCK cells under catalog number CCL-34. PER.C6 is available from the ECACC under deposit number 96022940. As a less-preferred alternative to mammalian cell lines, virus can be grown on avian cell lines [e.g. refs. 24-26], including cell lines derived from ducks (e.g. duck retina) or hens. Examples of avian cell lines include avian embryonic stem cells [24,27] and duck retina cells [25]. Suitable avian embryonic stem cells, include the EBx cell line derived from chicken embryonic stem cells, EB45, EB14, and EB14-074 [28]. Chicken embryo fibroblasts (CEF) may also be used.

The most preferred cell lines for growing influenza viruses are MDCK cell lines. The original MDCK cell line is available from the ATCC as CCL-34, but derivatives of this cell line may also be used. For instance, reference 16 discloses a MDCK cell line that was adapted for growth in suspension culture ('MDCK 33016', deposited as DSM ACC 2219). Similarly, reference 29 discloses a MDCK-derived cell line that grows in suspension in serum-free culture (13-702', deposited as FERM BP-7449). Reference 30 discloses non-tumorigenic MDCK cells, including 'MDCK-S' (ATCC PTA-6500), 'MDCK-SF101' (ATCC PTA-6501), 'MDCK-SF102' (ATCC PTA-6502) and 'MDCK-SF103' (PTA-6503). Reference 31 discloses MDCK cell lines with high susceptibility to infection, including 'MDCK.5F1' cells (ATCC CRL-12042). Any of these MDCK cell lines can be used.

Where virus has been grown on a mammalian cell line then products of the invention will advantageously be free from egg proteins (e.g. ovalbumin and ovomucoid) and from chicken DNA, thereby reducing potential allergenicity.

Hemagglutinin in cell-derived products of the invention can have a different glycosylation pattern from the patterns seen in egg-derived viruses. Thus the HA (and other glycoproteins) may include glycoforms that are not seen in chicken eggs. Useful HA includes canine glycoforms.

The absence of egg-derived materials and of chicken glycoforms provides a way in which vaccine prepared from viruses grown in cell culture can be distinguished from egg-derived products.

Where virus has been grown on a cell line then the culture for growth, and also the viral inoculum used to start the culture, will preferably be free from (i.e. will have been tested for and given a negative result for contamination by) herpes simplex virus, respiratory syncytial virus, parainfluenza virus 3, SARS coronavirus, adenovirus, rhinovirus, reoviruses, polyomaviruses, birnaviruses, circoviruses, and/or parvoviruses [32]. Absence of herpes simplex viruses is particularly preferred.

For growth on a cell line, such as on MDCK cells, virus may be grown on cells in suspension [16, 33, 34] or in adherent culture. One suitable MDCK cell line for suspension culture is MDCK 33016 (deposited as DSM ACC 2219). As an alternative, microcarrier culture can be used.

Cell lines supporting influenza virus replication are preferably grown in serum-free culture media and/or protein free media. A medium is referred to as a serum-free medium in the context of the present invention in which there are no additives from serum of human or animal origin. Protein-free is understood to mean cultures in which multiplication of the cells occurs with exclusion of proteins, growth factors, other protein additives and non-serum proteins, but can optionally include proteins such as trypsin or other proteases that may be necessary for viral growth. The cells growing in such cultures naturally contain proteins themselves.

Cell lines supporting influenza virus replication are preferably grown below 37° C. during viral replication e.g. 30-36° C., at 31-35° C., or at 33±1° C.

The method for propagating virus in cultured cells generally includes the steps of inoculating the cultured cells with the strain to be cultured, cultivating the infected cells for a desired time period for virus propagation, such as for example as determined by virus titer or antigen expression (e.g. between 24 and 168 hours after inoculation) and collecting the propagated virus. The cultured cells are inoculated with a virus (measured by PFU or $TCID_{50}$) to cell ratio of 1:500 to 1:1, preferably 1:100 to 1:5, more preferably 1:50 to 1:10. The virus is added to a suspension of the cells or is applied to a monolayer of the cells, and the virus is absorbed on the cells for at least 60 minutes but usually less than 300 minutes, preferably between 90 and 240 minutes at 25° C. to 40° C., preferably 28° C. to 37° C. The infected cell culture (e.g. monolayers) may be removed either by freeze-thawing or by enzymatic action to increase the viral content of the harvested culture supernatants. The harvested fluids are then either inactivated or stored frozen. Cultured cells may be infected at a multiplicity of infection ("m.o.i.") of about 0.0001 to 10, preferably 0.002 to 5, more preferably to to 2. Still more preferably, the cells are infected at a m.o.i of about 0.01. Infected cells may be harvested 30 to 60 hours post infection. Preferably, the cells are harvested 34 to 48 hours post infection. Still more preferably, the cells are harvested 38 to 40 hours post infection. Proteases (typically trypsin) are generally added during cell culture to allow viral release, and the proteases can be added at any suitable stage during the culture.

A vaccine product including vaccine prepared from cell culture preferably contains less than 10ng (preferably less than 1 ng, and more preferably less than 100 pg) of residual host cell DNA per dose, although trace amounts of host cell DNA may be present.

It is preferred that the average length of any residual host cell DNA is less than 500 bp e.g. less than 400 bp, less than 300 bp, less than 200 bp, less than 100 bp, etc.

Contaminating DNA can be removed during vaccine preparation using standard purification procedures e.g. chromatography, etc. Removal of residual host cell DNA can be enhanced by nuclease treatment e.g. by using a DNase. A convenient method for reducing host cell DNA contamination is disclosed in references 36 & 37, involving a two-step treatment, first using a DNase (e.g. Benzonase), which may be used during viral growth, and then a cationic detergent (e.g. CTAB), which may be used during virion disruption. Treatment with an alkylating agent, such as β-propiolactone, can also be used to remove host cell DNA, and advantageously may also be used to inactivate virions [38].

Some embodiments of the invention use a monovalent influenza vaccine (i.e. it includes hemagglutinin antigen from a single influenza virus strain) but in some embodiments it may be a multivalent vaccine, such as a bivalent vaccine, trivalent vaccine, a tetravalent vaccine, or a >4-valent vaccine (i.e. including hemagglutinin from more than four different influenza virus strains). Monovalent and multivalent vaccines are readily distinguished by testing for multiple HA types, by amino acid sequencing, etc.

A monovalent vaccine is particularly useful for immunising against a pandemic or potentially-pandemic strain, either during a pandemic or in a pre-pandemic situation. Characteristics of these strains are: (a) they contain a new hemagglutinin compared to the hemagglutinins in currently-circulating human strains, i.e. one that has not been evident in the human population for over a decade (e.g. H2), or has not previously been seen at all in the human population (e.g. H5, H6 or H9, that have generally been found only in bird populations), such that the human population will be immunologically naïve to the strain's hemagglutinin; (b) they are capable of being transmitted horizontally in the human population; and (c) they are pathogenic to humans. These strains may have any of influenza A HA subtypes H1, H2, H3, H4, H5, H6, H7, H8, H9, H10, H11, H12, H13, H14, H15 or H16. A virus with H5 hemagglutinin type is preferred for immunizing against pandemic influenza, or a H2, H7 or H9 subtype. The invention may protect against one or more of influenza A virus NA subtypes N1, N2, N3, N4, N5, N6, N7, N8 or N9. Thus possible strains include H5N1, H5N3, H9N2, H2N2, H7N1 and H7N7, and any other emerging potentially pandemic strains.

A multivalent vaccine is more typical in a seasonal setting e.g. a trivalent vaccine is typical, including hemagglutinins from two influenza A virus strains and one influenza B virus strain, such as from a H1N1 influenza A strain, a H3N2 influenza A virus strain, and an influenza B virus strain. A tetravalent vaccine is also useful e.g. including antigens from two influenza A virus strains and two influenza B virus strains, or three influenza A virus strains and one influenza B virus strain. Thus a vaccine may be bivalent, trivalent, tetravalent, etc. Except for monovalent vaccines, it is usual to include hemagglutinin from both influenza A and influenza B virus strains. In vaccines including only two influenza A virus strains, these will usually be one H1 strain (e.g. a H1N1 strain) and one H3 strain (e.g. a H3N2 strain). In some embodiments, however, there may be one pandemic influenza A virus strain and one H1 strain, or one pandemic influenza A virus strain and one H3 strain.

Where a vaccine includes more than one strain of influenza, the different strains are typically grown separately and are mixed after the viruses have been harvested and antigens have been prepared. Thus a process of the invention may include the step of mixing antigens from more than one influenza strain.

As described in reference 39, exemplary tetravalent vaccines can include hemagglutinin from two influenza A virus strains and two influenza B virus strains ('A-A-B-B'), or from three influenza A virus strains and one influenza B virus strain ('A-A-A-B').

Influenza B virus currently does not display different HA subtypes, but influenza B virus strains do fall into two distinct lineages. These lineages emerged in the late 1980s and have HAs which can be antigenically and/or genetically distinguished from each other [40]. Current influenza B virus strains are either B/Victoria/2/87-like or B/Yamagata/16/88-like. Where a vaccine of the invention includes two influenza B strains, this will usually be one B/Victoria/2/87-like strain and one B/Yamagata/16/88-like strain. These strains are usually distinguished antigenically, but differences in amino acid sequences have also been described for distinguishing the two lineages e.g. B/Yamagata/16/88-like strains often (but not always) have HA proteins with deletions at amino acid residue 164, numbered relative to the 'Lee40' HA sequence [41].

Preferred A-A-B-B vaccines include hemagglutinins from: (i) a H1N1 strain; (ii) a H3N2 strain; (iii) a B/Victoria/2/87-like strain; and (iv) B/Yamagata/16/88-like strain.

In vaccines including three influenza A virus strains, these will usually be one H1 strain (e.g. a H1N1 strain) and two H3 strains (e.g. two H3N2 strains). The two H3 strains will have antigenically distinct HA proteins e.g. one H3N2 strain that cross-reacts with A/Moscow/10/99 and one H3N2 strain that cross-reacts with A/Fujian/411/2002. The two H3 strains may be from different clades (clades A, B and C of H3N2 strains are disclosed in reference 42). In some embodiments, however, one of these strains (i.e. H1, or one of the two H3 strains) may be replaced by a pandemic strain.

Thus one preferred A-A-A-B vaccine includes hemagglutinins from: (i) a H1N1 strain; (ii) a A/Moscow/10/99-like H3N2 strain; (iii) a A/Fujian/411/2002-like H3N2 strain; and (iv) an influenza B virus strain, which may be B/Victoria/2/87-like or B/Yamagata/16/88-like.

Another preferred A-A-A-B vaccine includes hemagglutinins from: (i) a H1N1 strain, (ii) a H3N2 strain, (iii) a H5 strain (e.g. a H5N1 strain) and (iv) an influenza B strain.

Another preferred A-A-A-B vaccine includes hemagglutinins from: (i) two different H1 strains, (ii) a H3N2 strain, and (iii) an influenza B strain.

Where antigens are present from two or more influenza B virus strains, at least two of the influenza B virus strains may have distinct hemagglutinins but related neuraminidases. For instance, they may both have a B/Victoria/2/87-like neuraminidase or may both have a B/Yamagata/16/88-like neuraminidase. For instance, two B/Victoria/2/87-like neuraminidases may both have one or more of the following sequence characteristics: (1) not a serine at residue 27, but preferably a leucine; (2) not a glutamate at residue 44, but preferably a lysine; (3) not a threonine at residue 46, but preferably an isoleucine; (4) not a proline at residue 51, but preferably a serine; (5) not an arginine at residue 65, but preferably a histidine; (6) not a glycine at residue 70, but preferably a glutamate; (7) not a leucine at residue 73, but preferably a phenylalanine; and/or (8) not a proline at residue 88, but preferably a glutamine. Similarly, in some embodiments the neuraminidase may have a deletion at residue 43, or it may have a threonine; a deletion at residue 43, arising from a trinucleotide deletion in the NA gene, has been reported as a characteristic of B/Victoria/2/87-like strains, although recent strains have regained Thr-43 [43]. Conversely, of course, the opposite characteristics may be shared by two B/Yamagata/16/88-like neuraminidases e.g. S27, E44, T46, P51, R65, G70, L73, and/or P88. These amino acids are numbered relative to the 'Lee40' neuraminidase sequence [44]. Thus a A-A-B-B vaccine of the invention may use two B strains that are antigenically distinct for HA (one B/Yamagata/16/88-like, one B/Victoria/2/87-like), but are related for NA (both B/Yamagata/16/88-like, or both B/Victoria/2/87-like).

Strains whose antigens can usefully be included in the compositions include strains which are resistant to antiviral therapy (e.g. resistant to oseltamivir and/or zanamivir), including resistant pandemic strains [46].

In some embodiments a vaccine of the invention may include a small amount of mercury-based preservative, such as thiomersal or merthiolate. When present, such preservatives will typically provide less than 5 µg/ml mercury, and lower levels are possible e.g. <1 µg/ml, <0.5 µg/ml. Preferred vaccines are free from thiomersal, and are more preferably mercury-free [8,47]. Such vaccines may include a non-mercurial preservative. Non-mercurial alternatives to thiomersal include 2-phenoxyethanol or α-tocopherol succinate [8]. Most preferably, a vaccine is preservative-free.

In some embodiments, a vaccine may include a stabilising amount of gelatin e.g. at less than 0.1%. In other embodiments, however, a vaccine is gelatin-free. The absence of gelatin can assure that the vaccine is safe in the small proportion of subjects who are gelatin-sensitive [48,49].

In some embodiments, a vaccine may include one or more antibiotics e.g. neomycin, kanamycin, polymyxin B. In preferred embodiments, though, the vaccine is free from antibiotics.

In some embodiments, a vaccine may include formaldehyde. In preferred embodiments, though, the vaccine is free from formaldehyde.

As mentioned above, in some embodiments a vaccine may include egg components (e.g. ovalbumin and ovomucoid), but preferred embodiments are free from egg components.

The preparation of vaccines without the use of certain components and additives is disclosed in reference 50, thereby ensuring that these materials are not present even in residual amounts.

Hemagglutinin (HA) is the main immunogen in current inactivated influenza vaccines, and vaccine doses are standardised by reference to HA levels, typically measured by SRID. Existing vaccines typically contain about 15 µg of HA per strain, although lower doses can be used e.g. for children, or in pandemic situations, or when using an adjuvant. Fractional doses such as ½ (i.e. 7.5 µg HA per strain), ¼ and ⅛ have been used, as have higher doses (e.g. 3×, 4× or 9× doses [51,52]). These vaccines have a dosage volume of 0.5 ml i.e. a typical HA concentration of 30 µg/ml/strain. The trivalent INTANZA™ product contains 9 µg of HA per strain in a 0.1 ml volume i.e. a HA concentration of 90 µg/ml/strain, giving a total HA concentration of 270 µg/ml.

Products of the present invention can include between 0.1 and 150 µg of HA per influenza strain per dose, preferably between 0.1 and 50 µg e.g. 1-20 µg. Ideally a product has ≤16 µg hemagglutinin per strain e.g. 1-15 µg, 1-10 µg, 1-7.5 µg, 1-5 µg, etc. Particular HA doses per strain include e.g. about 60, about 45, about 30, about 15, about 10, about 7.5, about 5, about 3.8, about 1.9, about 1.5, etc.

For live vaccines, dosing is measured by median tissue culture infectious dose ($TCID_{50}$) rather than HA content e.g. a $TCID_{50}$ of between $10^6$ and $10^8$ (preferably between $10^{6.5}$-$10^{7.5}$) per strain per dose.

Influenza strains used with the invention may have a natural HA as found in a wild-type virus, or a modified HA. For instance, it is known to modify HA to remove determinants (e.g. hyper-basic regions around the HA1/HA2 cleavage site) that cause a virus to be highly pathogenic in avian species. The use of reverse genetics facilitates such modifications.

Vaccine products may include a detergent. The level of detergent can vary widely e.g. between 0.05-50 µg detergent per µg of HA ('µg/µg'). A low level of detergent can be used e.g. between 0.1-1 µg/µg, or a high level can be used e.g. between 5-30 µg/µg. The detergent may be a single detergent (e.g. polysorbate 80, or CTAB) or a mixture (e.g. both polysorbate 80 and CTAB). Preferred detergents are non-ionic, such as polysorbate 80 ('Tween 80') or octyl phenol ethoxylate ('Triton X100'). Polysorbate 80 may be present at between 0.05-50 µg polysorbate 80 per µg of HA e.g. between 0.1-1 µg/µg, 0.1-0.8 µg/µg, 0.1-0.5 µg/µg, 5-40 µg/µg, 5-30 µg/µg, or 8-25 µg/µg. Vaccine products may include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Vaccine products may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

Vaccine products are preferably sterile. Vaccine products are preferably non-pyrogenic e.g. containing <1 EU (endotoxin unit, a standard measure) per dose, and preferably <0.1 EU per dose. Vaccine products are preferably gluten-free.

Vaccine products can include immunostimulatory molecules. These can be mixed with antigen before preparing a patch. Suitable classes of immunostimulatory molecule include, but are not limited to: TLR3 agonists; TLR4 agonists; TLR5 agonists; TLR7 agonists; TLR8 agonists; TLR9 agonists; and CD1d agonists. Suitable immunostimulatory molecules include, but are not limited to: imidazoquinolines such as imiquimod ("R-837") [53,54] and resiquimod ("R-848") [55], or salts thereof (e.g. the hydrochloride salts); aminoalkyl glucosaminide phosphate derivatives, such as RC-529 [56,57]; α-glycosylceramides, such as α-galactosylceramide; 'ER 804057' from reference 58; E5564 [59, 60]; etc.

Methods for assessing antibody responses, neutralising capability and protection after influenza virus vaccination are well known in the art. Human studies have shown that antibody titers against hemagglutinin of human influenza virus are correlated with protection (a serum sample hemagglutination-inhibition titer of about 30-40 gives around 50% protection from infection by a homologous virus) [61]. Antibody responses are typically measured by hemagglutination inhibition, by microneutralization, by single radial immunodiffusion (SRID), and/or by single radial hemolysis (SRH). These assay techniques are well known in the art. Preferred vaccines satisfy 1, 2 or 3 of the CPMP criteria for efficacy. In elderly (>60 years), these criteria are: (1) ≥60% seroprotection; (2) ≥30% seroconversion; and/or (3) a GMT increase of ≥2-fold. These criteria are based on open label studies with at least 50 subjects.

The vaccine may be administered as a single dose or as a series of doses. Administration of more than one dose (typically two doses) is particularly useful in immunologically naïve subjects e.g. for people who have never received an influenza vaccine before, or for vaccinating against a new HA subtype (as in a pandemic outbreak).

A typical dosage volume for a human influenza vaccine is 0.5 ml, but the invention can use smaller or larger volumes. For instance, the vaccine can be administered as a unit dosage volume of between 0.05 ml and 1.0 ml e.g. 0.1 ml, 0.25 m, 0.5 ml, or 0.75 ml. Antigen concentration will be adapted accordingly to provide the desired final antigen dose. A 0.5 ml dosage volume is preferred.

A vaccine will typically be distributed inside a container. Suitable containers for the vaccines include vials, nasal sprays and disposable syringes, which should be sterile.

Where a composition/component is located in a vial, the vial is preferably made of a glass or plastic material. The vial is preferably sterilized before the composition is added to it. To avoid problems with latex-sensitive patients, vials are preferably sealed with a latex-free stopper, and the absence of latex in all packaging material is preferred. The vial may include a single dose of vaccine, or it may include more than one dose (a 'multidose' vial) e.g. 10 doses. Preferred vials are made of colorless glass.

A vial can have a cap (e.g. a Luer lock) adapted such that a pre-filled syringe can be inserted into the cap, the contents of the syringe can be expelled into the vial, and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed. A vial may have a cap that permits aseptic removal of its contents, particularly for multidose vials.

Where a composition/component is packaged into a syringe, the syringe may have a needle attached to it. If a needle is not attached, a separate needle may be supplied with the syringe for assembly and use. Such a needle may be sheathed. Safety needles are preferred. 1-inch 23-gauge, 1-inch 25-gauge and ⅝-inch 25-gauge needles are typical. Syringes may be provided with peel-off labels on which the lot number, influenza season and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of a butyl rubber. If the syringe and needle are packaged separately then the needle is preferably fitted with a butyl rubber shield. Preferred syringes are those marketed under the trade name "Tip-Lok" ™.

Containers may be marked to show a half-dose volume e.g. to facilitate delivery to children. For instance, a syringe containing a 0.5 ml dose may have a mark showing a 0.25 ml volume.

Where a glass container (e.g. a syringe or a vial) is used, then it is preferred to use a container made from a borosilicate glass rather than from a soda lime glass.

A composition may be combined (e.g. in the same box) with a leaflet including details of the vaccine e.g. instructions for administration, details of the antigens within the vaccine, etc. The instructions may also contain suitable product warnings.

The Adjuvant

Vaccines of the invention include an adjuvant. Various suitable adjuvants are known, but a typical adjuvant comprises an oil-in-water emulsion. Various suitable emulsions are known, and they typically include at least one oil and at least one surfactant, with the oil(s) and surfactant(s) being biodegradable (metabolizable) and biocompatible. The oil droplets in the emulsion are generally less than 5 μm in diameter, and advantageously the emulsion comprises oil droplets with a sub-micron diameter, with these small sizes being achieved with a microfluidizer to provide stable emulsions. Droplets with a size less than 220 nm are preferred as they can be subjected to filter sterilization.

The emulsion can include oils from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolisable and may therefore be used in the practice of this invention. The procedures for separation, purification, saponification and other means necessary for obtaining pure oils from animal sources are well known in the art. Most fish contain metabolisable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoid known as squalene, 2,6,10,15,19,23-hexamethyl-2,6,10,14,18,22-tetracosahexaene. Other preferred oils are the tocopherols, including DL-α-tocopherol. Oil-in-water emulsions comprising squalene are particularly preferred. Mixtures of oils can be used.

Surfactants can be classified by their 'HLB' (hydrophile/lipophile balance). Preferred surfactants of the invention have a HLB of at least 10, preferably at least 15, and more preferably at least 16. Examples of suitable surfactants include, but are not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Preferred surfactants for including in the emulsion are Tween 80 (polyoxyethylene sorbitan monooleate; polysorbate 80), Span 85 (sorbitan trioleate), lecithin and Triton X-100. Inclusion of polysorbate 80 is preferred.

Mixtures of surfactants can be used e.g. Tween 80/Span 85 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Specific oil-in-water emulsion adjuvants useful with the invention include, but are not limited to:

A submicron emulsion of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' [62-64], as described in more detail in Chapter 10 of ref. 65 and chapter 12 of ref. 66. The MF59 emulsion advantageously includes citrate ions e.g. 10 mM sodium citrate buffer.

An emulsion comprising squalene, an α-tocopherol, and polysorbate 80. These emulsions may have from 2 to 10% squalene, from 2 to 10% tocopherol and from 0.3 to 3% Tween 80, and the weight ratio of squalene: tocopherol is preferably ≤1 (e.g. 0.90) as this provides a more stable emulsion. Squalene and Tween 80 may be present at a volume ratio of about 5:2, or at a weight ratio of about 11:5. One such emulsion can be made by dissolving Tween 80 in PBS to give a 2% solution, then mixing 90 ml of this solution with a mixture of (5 g of DL-α-tocopherol and 5 ml squalene), then microfluidizing the mixture. The resulting emulsion may have submicron oil droplets e.g. with an average diameter of between 100 and 250 nm, preferably about 180 nm.

An emulsion of squalene, a tocopherol, and a Triton detergent (e.g. Triton X-100). The emulsion may also include a 3d-MPL (see below). The emulsion may contain a phosphate buffer.

An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 μg/ml polysorbate 80, 110 μg/ml Triton X-100 and 100 μg/ml α-tocopherol succinate), and these concentrations should include any contribution of these components from antigens. The emulsion may also include squalene. The emulsion may also include a 3d-MPL (see below). The aqueous phase may contain a phosphate buffer.

An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant [67] (0.05-1% Thr-MDP, 5% squalane, 2.5% Pluronic L121 and 0.2% polysorbate 80). It can also be used without the Thr-MDP, as in the "AF" adjuvant [68] (5% squalane, 1.25% Pluronic L121 and 0.2% polysorbate 80). Microfluidization is preferred.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm [69]. The emulsion may also include one or more of: alditol; a cryoprotective agent (e.g. a sugar, such as dodecylmaltoside and/or sucrose); and/or an alkylpolyglycoside. The emulsion may include a TLR4 agonist [70]. Such emulsions may be lyophilized.

An emulsion having from 0.5-50% of an oil, 0.1-10% of a phospholipid, and 0.05-5% of a non-ionic surfactant. As described in reference 71, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolisable oil (such as light mineral oil) and at least one surfactant (such as lecithin, Tween 80 or Span 80). Additives may be included, such as QuilA saponin, cholesterol, a saponin-lipophile conjugate (such as GPI-0100, described in reference 72, produced by addition of aliphatic amine to desacylsaponin via the carboxyl group of glucuronic acid), dimethyidioctadecylammonium bromide and/or N,N-dioctadecyl-N, N-bis (2-hydroxyethyl)propanediamine.

An emulsion comprising a mineral oil, a non-ionic lipophilic ethoxylated fatty alcohol, and a non-ionic hydrophilic surfactant (e.g. an ethoxylated fatty alcohol and/or polyoxyethylene-polyoxypropylene block copolymer) [73].

An emulsion comprising a mineral oil, a non-ionic hydrophilic ethoxylated fatty alcohol, and a non-ionic lipophilic surfactant (e.g. an ethoxylated fatty alcohol and/or polyoxyethylene-polyoxypropylene block copolymer) [73].

An emulsion in which a saponin (e.g. QuilA or QS21) and a sterol (e.g. a cholesterol) are associated as helical micelles [74].

Antigens and adjuvants in a composition will typically be in admixture at the time of delivery to a subject. The emulsions may be mixed with antigen during manufacture, or extemporaneously, at the time of delivery. Thus the adjuvant and antigen may be kept separately in a packaged or distributed vaccine, ready for final formulation at the time of use. The antigen will generally be in an aqueous form, such that the vaccine is finally prepared by mixing two liquids. The volume ratio of the two liquids for mixing can vary (e.g. between 5:1 and 1:5) but is generally about 1:1. Thus an antigen-containing composition may include a higher concentration of antigen than will be administered to a subject e.g. a 2× concentration for 1:1 dilution with adjuvant to give the final desired concentration. Similarly, the final desired antigen dose may be contained in a smaller volume than the final administration volume e.g. the desired dose may be in a 0.25 ml volume for 1:1 dilution with adjuvant to give the final desired 0.5 ml dosage volume.

After the antigen and adjuvant have been mixed, haemagglutinin antigen will generally remain in aqueous solution but may distribute itself around the oil/water interface. In general, little if any haemagglutinin will enter the oil phase of the emulsion.

Where a composition includes a tocopherol, any of the a, P, y, 6, c or tocopherols can be used, but α-tocopherols are preferred. The tocopherol can take several forms e.g. different salts and/or isomers. Salts include organic salts, such as succinate, acetate, nicotinate, etc. D-α-tocopherol and DL-α-tocopherol can both be used. Tocopherols are advantageous because vitamin E has been reported to have a positive effect on the immune response in elderly subjects [75]. They also have antioxidant properties that may help to stabilize the emulsions [76]. A preferred α-tocopherol is DL-α-tocopherol, and the preferred salt of this tocopherol is the succinate. The succinate salt has been found to cooperate with TNF-related ligands in vivo. Moreover, α-tocopherol succinate is known to be compatible with influenza vaccines and to be a useful preservative as an alternative to mercurial compounds.

As mentioned above, oil-in-water emulsions comprising squalene are particularly preferred. In some embodiments, the squalene concentration in a vaccine dose may be in the range of 5-15 mg (i.e. a concentration of 10-30 mg/ml, assuming a 0.5 ml dose volume). It is possible, though, to reduce the concentration of squalene [77,78] e.g. to include <5 mg per dose, or even <1.1 mg per dose. For example, a human dose may include 9.75 mg squalene per dose (as in the FLUAD™ product: 9.75 mg squalene, 1.175 mg polysorbate 80, 1.175 mg sorbitan trioleate, in a 0.5 ml dose volume), or it may include a fractional amount thereof e.g. ¾, ⅔, ½, ⅓, ¼, ⅕, ⅙, ⅐, ⅛, ⅑, or ⅒. For example, a composition may include 7.31 mg squalene per dose (and thus 0.88 mg each of polysorbate 80 and sorbitan trioleate), 4.875 mg squalene/dose (and thus 0.588 mg each of polysorbate 80 and sorbitan trioleate), 3.25 mg squalene/dose, 2.438 mg/dose, 1.95 mg/dose, 0.975 mg/dose, etc. Any of these fractional dilutions of the FLUAD™-strength MF59 can be used with the invention.

As mentioned above, antigen/emulsion mixing may be performed extemporaneously, at the time of delivery. Thus the invention provides kits including the antigen and adjuvant components ready for mixing. The kit allows the adjuvant and the antigen to be kept separately until the time of use. The components are physically separate from each other within the kit, and this separation can be achieved in various ways. For instance, the two components may be in two separate containers, such as vials. The contents of the two vials can then be mixed e.g. by removing the contents of one vial and adding them to the other vial, or by separately removing the contents of both vials and mixing them in a third container. In a preferred arrangement, one of the kit components is in a syringe and the other is in a container such as a vial. The syringe can be used (e.g. with a needle) to insert its contents into the second container for mixing, and the mixture can then be withdrawn into the syringe. The mixed contents of the syringe can then be administered to a subject, typically through a new sterile needle. Packing one component in a syringe eliminates the need for using a separate syringe for subject administration. In another preferred arrangement, the two kit components are held together but separately in the same syringe e.g. a dual-chamber syringe, such as those disclosed in references 79-86 etc. When the syringe is actuated (e.g. during administration to a subject) then the contents of the two chambers are mixed. This arrangement avoids the need for a separate mixing step at the time of use.

Risk Reduction

The invention reduces a subject's risk of hospitalization for respiratory illness e.g. for influenza and/or pneumonia. This reduction is measured relative to an elderly subject who receives an unadjuvanted influenza vaccine. For instance, two vaccines can be prepared which are identical except that one includes adjuvant i.e. their dosage volume, amount of antigen, virus strains, antigen type and non-adjuvant excipients are the same. Administration of the adjuvanted vaccine to a population of elderly subjects (a first population) leads to a lower rate of hospitalization for respiratory illness (e.g. for influenza and/or pneumonia) than is seen in a corresponding population of elderly subjects (a second population) who instead receives the unadjuvanted vaccine, and so the risk of hospitalization for a member of the first population is lower the risk for a member of the second population.

An elderly subject is hospitalized for respiratory illness if they are admitted to hospital and are diagnosed therein as having a respiratory illness. This diagnosis can be an admission diagnosis but will typically be a discharge diagnosis. Diagnosis of respiratory illness can be made according to the International Classification of Disease system ("ICD"), and is conveniently made under its ICD-9 or ICD-9-CM systems (ninth revision), the latter of which is administered by the National Center for Health Statistics (NCHS) and the Centers for Medicare and Medicaid Services. ICD-9-CM codes 460 to 519 are for respiratory illnesses.

An elderly subject is hospitalized for influenza or pneumonia if they are admitted to hospital and are diagnosed therein as having influenza or pneumonia. This diagnosis can be an admission diagnosis but will typically be a discharge diagnosis. Diagnosis of influenza or pneumonia can be made according to the ICD system. ICD-9-CM codes 480 to 488 are for influenza and pneumonia:
- 480=Viral pneumonia
- 481=Pneumococcal pneumonia [*Streptococcus pneumoniae* pneumonia]
- 482=Other bacterial pneumonia
- 483=Pneumonia due to other specified organism
- 484=Pneumonia in infectious diseases classified elsewhere
- 485=Bronchopneumonia organism unspecified
- 486=Pneumonia organism unspecified
- 487=Influenza
- 488=Influenza due to identified avian influenza virus Under the tenth revision of the ICD ("ICD-10") the codes for respiratory illnesses are in Chapter X (the block consisting of J00 to J99); the ICD-10 codes for influenza and pneumonia are the block consisting of J09 to J18.

Thus a subject's risk of being hospitalised and diagnosed with an ICD-9-CM code of 460-519 and/or of an ICD-10 code in block J00-J99 is reduced after receiving an adjuvanted influenza vaccine according to the invention. In some embodiments, a subject's risk of being hospitalised and diagnosed with an ICD-9-CM code of 480-488 and/or of an ICD-10 code in block J09-J18 is reduced after receiving an adjuvanted influenza vaccine according to the invention.

The risk reduction achieved with the invention is particularly useful in the peak influenza season (e.g. in December to February in the northern hemisphere).

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±5%.

Where animal (and particularly bovine) materials are used in the culture of cells, they should be obtained from sources that are free from transmissible spongiform encephalopathies (TSEs), and in particular free from bovine spongiform encephalopathy (BSE). Overall, it is preferred to culture cells in the total absence of animal-derived materials.

DETAILED EMBODIMENTS OF THE INVENTION

Comparative studies in the community have generally found that conventional influenza vaccines are modestly effective in preventing hospitalization and mortality in the elderly during the influenza season [2]. The Italian National Healthcare System (INHS) provided an opportunity to evaluate adjuvanted influenza vaccines in a field setting. The INHS is decentralized with health services, data collection and validation coordinated at the regional level. The healthcare data are accessible and can be used for pharmacoepidemiologic studies.

Current Italian guidelines on the prevention and control of influenza provide free access to vaccines for those at high risk for complications, including the elderly—for whom the use of either conventional or adjuvanted formulations is approved—with adjuvanted vaccine generally recommended by the Ministry of Health for more frail people. In the absence of clear effectiveness data for the adjuvanted vaccine a population-based cohort study of adjuvanted versus conventional influenza vaccine has been performed during three consecutive influenza seasons starting in the fall of 2006, in five provinces in Northern Italy (Lombardy region). The primary objective was to assess the occurrence of hospitalization for influenza-related conditions. The resulting study is the first large-scale study of the comparative effectiveness and safety of two influenza vaccine formulations.

A prospective cohort study was conducted among the residents of the provinces of Cremona, Bergamo, Mantova, Lecco and Pavia who were at least 65 years old and who received influenza vaccines which differ only by the presence or absence of an adjuvant—the adjuvanted Fluad™ vaccine or the conventional Agrippal™ vaccine. The vaccines contained the WHO-recommended strains for the respective influenza season in the Northern Hemisphere. The study excluded residents who were in hospital, nursing homes, or rehabilitation centers in the 30 days preceding immunization, as well as those receiving home care or who reported that they were intolerant of influenza vaccines.

There was no attempt at random assignment of vaccines, but both types of vaccine were distributed to residents through either General Practitioners (GP) or District offices in each local health authority (LHA) according to the local implementation of regional influenza vaccination policy in line with national recommendations. A vaccination registry was created for the study. All vaccine recipients were asked for their informed consent to participate in the study; those who accepted were administered a brief questionnaire to record the basic demographic data, and information on potential confounders, including smoking status, functional status (based on self-reported answers to questions about physical capabilities), presence of children in the household and having been vaccinated for influenza the previous year.

For each enrolled subject, residence status was confirmed through record linkage with administrative databases; all failures were excluded from the study. Subsequently, the presence of chronic disease or other relevant routinely collected medical history information was ascertained through record linkage with databases containing data on hospitalizations (discharge diagnoses), outpatient drug prescriptions (active ingredient and estimated duration of treatment), ambulatory care with specialist, and certified exemption from copayment of healthcare costs.

The primary outcome was defined as any discharge diagnoses for influenza or pneumonia after hospitalization (ICD-9-CM codes 480-488) during influenza season, recorded in the hospital database. Influenza season was defined on the basis of a nationwide surveillance network ("Influnet") that monitors influenza occurrence in Italy each year and includes 1,000 GPs and family pediatricians; the network provides weekly incidence data, stratified by age and region. Data were pooled over the three influenza seasons, such that the elementary data record was a "person-season" at risk. Because many people were included for more than one of the three years of observation, a generalized estimating equation (GEE) was used to take account of the correlation induced by measuring the experience of the same people for more than one influenza season.

The case definition did not require a positive finding for influenza virus. Therefore, in order to increase the specificity of the identification of cases hospitalized for influenza-related conditions, three different influenza time windows were defined during which hospitalizations were counted.

The broadest risk window corresponded to the entire influenza season, as determined from Influnet.

The narrower risk window corresponded to the period of adjacent weeks around the peak influenza occurrence of each season, with all weeks in the window having an influenza rate that exceeded 1 per 1000 person-weeks. An intermediate risk window was defined in the same way but with a threshold of 0.5 cases per 1000 person-weeks. The broader windows capture more cases, but are less specific for influenza-related cases and would bias results toward the null. The primary focus was on the results using the narrower window, with greatest specificity and least bias toward the null.

Also, in order to estimate the amount of potential misclassification of the discharge diagnosis, a sample of hospital discharge records in Cremona was validated and the diagnosis matched with automated hospital discharge diagnoses.

To assess and control confounding, stratification was coupled with Mantel-Haenszel summary estimates of a pooled effect measure. Variables assessed as potential confounders included age, gender, influenza season, LHA and vaccine provider, physical impairment, smoking, recent infectious disease, transfusion, intestinal disorder, self-reported flu symptoms, infectious disease, and chronic conditions such as COPD, kidney disease, diabetes, cardiovascular disease, peripheral vascular disease, cancer, and history of hospitalization for pneumonia, influenza or emphysema. Every potential confounder in stratified analyses could not be simultaneously controlled and so a multivariate analysis was used with a propensity score as a summary confounding score. A logistic regression model was used to estimate the probability of receiving either vaccine. Variables that were included in this model included age, sex, influenza season, community and provider, physical impairment, smoking, presence of children in the home, recent transfusion, recent intestinal disorder, recent self-reported flu symptoms, recent infectious disease, history of hospitalization for pneumonia, influenza or emphysema, COPD, diabetes, cardiovascular disease, chronic kidney disease, peripheral vascular disease, and cancer. First, to avoid including nonconfounding predictors of exposure, which would not reduce confounding but would decrease precision, a preliminary logistic model predicting hospitalization with influenza-like illness that included all these covariates, along with study vaccine, was fitted to determine the strength of relation of each variable with the study outcome. As a second stage, the model was fitted to predict study vaccine assignment (the propensity score model) using those predictors from the preliminary outcome model that had a relative risk of at least 1.4: age, sex, influenza season, community and provider, physical impairment, history of hospitalization for pneumonia, influenza or emphysema, COPD, chronic kidney disease, diabetes, recent infectious disease, and recent transfusion. This fitted model was used to compute the propensity to receive Fluad™ for each person-season of observation, and added that to the data as an additional, derived variable. Because the propensity score predicts which vaccine was received, those receiving Fluad™ had a different distribution of scores from those receiving Agrippal™. To improve comparability of the two vaccine groups, the propensity score was controlled in multivariate models, but first all outlier observations were excluded ("trimming"), defined as those below the lower 2.5% of the tail of the Agrippal™ observations (3565 observations), and above the upper 2.5% tail of the Fluad™ observations (2931 observations). These tails are outside the primary area of overlap of the propensity scores, and increase residual confounding in any type of analysis.

The multivariate analyses employed GEE to account for the inclusion of people in more than one season. The final multivariate analysis was based on doubly robust estimation, in which the strongest confounders and the propensity score based on all confounders were included in the logistic model; this model in principle should provide the best control of confounding achievable with these data [87]. Statistical analysis was performed using SAS 9.1. Multiple imputation (Proc MI and Proc MIANALYZE) handled missing values, with 5 imputations.

A total of 107661 people fulfilled the study eligibility criteria, but the unit of analysis was person-season or, equivalently, the number of vaccinations provided. A person could contribute up to three separate influenza seasons of risk for influenza-related outcomes, each of the three having either vaccine assignment. Overall, 43667 participants were included for more than one year; of these 23484 received at least one vaccination of each type. The total number of person-seasons studied was 170988. These were distributed as shown in Table 1. After data trimming based on the propensity score distributions, 164007 person-seasons remained for analysis.

As expected, given the observational nature of the study and the implementation of regional recommendations on the preferential use of adjuvanted influenza vaccines in high risk groups, the two vaccine groups show some imbalance with respect to age, functional limitations and the prevalence of chronic conditions (See Table 2).

Based on influenza incidence in Lombardy during the three study years the narrower definition of the risk window for influenza-related events, which should have the greatest specificity for the outcomes of interest, corresponded to calendar weeks 4-7 inclusive in 2006-7, and weeks 52-4 and 1-7 for the subsequent two influenza seasons. During these periods there were a total of 115 hospitalizations for influenza and pneumonia among the 84,564 person-seasons at risk for the Fluad™ group (0.136%), compared with 112 among 79,443 for the Agrippal™ group (0.141%). The crude risk ratio was 0.96, with 95% confidence interval (CI) 0.74-1.25.

These crude comparisons are confounded by the various factors that are imbalanced between the two vaccine groups. Confounding was controlled for by LHA-provider and age using simultaneous stratification by these two variables. The stratified data are given in Table 3, which shows the distribution of person-seasons by age and LHA-provider for each of the two study groups. These stratum-specific results were summarised using the Mantel-Haenszel summary risk ratio (RR). This adjustment resulted in a RR estimate of 0.85 (95% CI of 0.65-1.11). This stratification was then extended to include sex, history of lung-related hospitalization, level of functional impairment, and season. The Mantel-Haenszel summary RR was then 0.79 (95% CI of 0.60-1.05). These analyses indicated that there was substantial confounding in the crude data, but with control of the main confounders, the adjuvanted vaccine group seemed to have about a 20% lower risk of hospitalizations for influenza and pneumonia.

The propensity score was then used as a summary confounder in a multivariate logistic analysis, based on the trimmed data, to control for any residual confounding. The "doubly robust" approach was used, which fits a model that includes the strongest confounders along with the propensity score. This model estimated a risk ratio of 0.77 (95% CI 0.59-0.99) for Fluad™ relative to Agrippal™ slightly stronger but not very different from the results of the stratified analyses (Table 4).

The above analyses were repeated using the intermediate and broader risk windows. These analyses have a less specific outcome than the analysis using the narrow risk window for influenza-related hospitalizations as they include a relatively greater proportion of background hospitalizations as the influenza epidemic began or waned. Thus one would expect that there would be more cases, but that the associations found would be attenuated. As expected, the number of cases increased from 227 for the analysis using the narrow risk window to 370 for the intermediate window and 742 for the broadest risk window. Also as expected, the risk ratio estimate, which was 0.77 for the narrow risk window, was attenuated to 0.85 for the intermediate window and 0.91 for the broadest window (Table 5).

With respect to the validation of hospital records in a subset of cases, the concordance between diagnosis in the medical records and diagnosis code in the database was confirmed in 99.4% of the sample.

This is the first large-scale study of the comparative effectiveness of an adjuvanted versus non adjuvanted influenza vaccine formulation. The large study population, comprising 107661 people who contributed 170988 person-seasons of observation, is considerably larger than could have been readily enrolled into a randomized trial. The study was able to link participants to available administrative data, combining both self-reported information through questionnaire with retrospective data on hospitalizations and drug prescriptions from administrative databases (extended to several years prior to enrolment). By extending the study over three years the year-to-year variation in the antigenic "match" between the vaccine and circulating influenza strains (a problem that hampers the interpretation of findings in any study based on only one influenza season) was reduced.

The crude comparison of those receiving Fluad™ and Agrippal™ showed little association, but this crude relation was confounded by differences in age and some other variables that differed between the two groups. Stratifying by age and community group removed most of the confounding, and gave results similar to the multivariate doubly robust model, which showed a risk ratio estimate of 0.77, equivalent to a 23% lower risk of hospitalization for respiratory problems among those receiving Fluad™, after controlling for propensity score. Methodologic research has shown that controlling confounding by propensity scores performs only about as well as more traditional methods [88]. Nevertheless, one advantage of calculating propensity scores is the ability to identify and exclude outliers from the two study groups who have propensity scores outside the range, or the central distribution, of the other group. This "trimming" improves validity of any analyses by restricting the study to comparable observations. The present study used trimming by propensity score as an initial step, followed by two methods to control confounding, stratification on the individual covariates, and doubly robust multivariate modeling.

Some non-experimental studies of influenza vaccine efficacy in preventing deaths have been saddled with selection bias, raising controversies about the validity of the observational approach in assessing influenza vaccine effectiveness [89-96]. This bias most likely reflects a "healthy-vaccinee" effect, in which those who are at high risk of a near-term death are less likely to be vaccinated. Such confounding bias should be less prominent in the present study, which considered hospitalization for influenza or pneumonia instead of mortality, and involved a head-to-head comparison of two influenza vaccines. Although this study did not involve random assignment, the confounding that was present was considerably less than the bias afflicting studies such as in reference 89. The baseline differences in risk factors that led to the comparatively modest confounding in this study were the result of the combination of chance and possibly haphazard allocation of vaccines within the study sites, with the tendency to select older or slightly more severe patients in the Fluad™ cohort in some LHA; however, these differences were most likely controllable in the data analysis. It is noteworthy that the crude baseline risk of hospitalization outside of influenza season (May-September) was 50% higher in the Fluad™ cohort. Therefore, if any residual selection bias was present in the estimates during influenza season, the estimates should be regarded as conservative since such bias would drive the result towards a lower effectiveness of Fluad™.

With respect to the lack of laboratory confirmation for the presence of influenza infection among the cases, once again the estimated 23% reduction in the risk of hospitalization in the group vaccinated with Fluad™ during the peak influenza season can be regarded as conservative because any residual non-differential misclassification of outcome would drive the estimate towards the null value. This is well represented in Table 5 where, after taking into account confounding, the estimated reduction with Fluad™ increases as the risk window narrows around the influenza peak, thus removing a greater proportion of "background" cases not specifically related to influenza.

In conclusion, vaccination with Fluad™ instead of Agrippal™, which differ only by the presence/absence of adjuvant, appears to reduce the risk of hospitalization for influenza and pneumonia in the elderly during the peak of the influenza season, and the best estimate of the reduced risk is 23%.

Further evidence in support of the invention was presented at the Fourth ESWI Influenza Conference held from 11th-14 Sep. 2011 in Malta. Mannino et al. [97] concluded that, during the peak of the influenza season, MF59-adjuvanted influenza vaccine reduced the risk of hospitalization due to all respiratory illnesses in the elderly by 21% when compared with non-adjuvanted influenza vaccine. If the time window was extended to the whole influenza season the effect of the adjuvant was reduced to 7%, but this reduction is unsurprising due to the reduced frequency of vaccine-modifiable respiratory conditions at the end of the influenza season. These observations are in line with the results of the results above which looked only at hospitalization due to influenza and pneumonia, and they support the suitability of the adjuvanted vaccine as a more effective influenza vaccine for adults aged 65 years or older.

It will be understood that the invention has been described by way of example only and modifications may be made whilst remaining within the scope and spirit of the invention.

[1] Durando et al. (2010) *Expert Opin Biol Ther.* 10(4):639-51.
[2] Jefferson et al. (2010) *Cochrane Database Syst Rev.* 17(2):CD004876.
[3] Vaccines. (eds. Plotkin & Orenstein). 4th edition, 2004, ISBN: 0-7216-9688-0.
[4] WO02/28422.
[5] WO02/067983.
[6] WO02/074336.
[7] WO01/21151.
[8] WO02/097072.
[9] WO2005/113756.
[10] Huckriede et al. (2003) *Methods Enzymol* 373:74-91.
[11] WO96/37624.
[12] WO98/46262.
[13] WO95/18861.
[14] Bright et al. (2008) *PLoS ONE* 3:e1501.
[15] Crevar & Ross (2008) *Virology Journal* 5:131.
[16] WO97/37000.
[17] Brands et al. (1999) *Dev Biol Stand* 98:93-100.
[18] Halperin et al. (2002) *Vaccine* 20:1240-7.
[19] Tree et al. (2001) *Vaccine* 19:3444-50.
[20] Kistner et al. (1998) *Vaccine* 16:960-8.
[21] Kistner et al. (1999) *Dev Biol Stand* 98:101-110.
[22] Bruhl et al. (2000) *Vaccine* 19:1149-58.
[23] Pau et al. (2001) *Vaccine* 19:2716-21.
[24] WO03/076601.
[25] WO2005/042728.
[26] WO03/043415.
[27] WO01/85938.
[28] WO2006/108846.
[29] EP-A-1260581 (WO01/64846).
[30] WO2006/071563.
[31] WO2005/113758.
[32] WO2006/027698.
[33] WO03/023021
[34] WO03/023025
[35] WO97/37001.
[36] EP-B-0870508.
[37] U.S. Pat. No. 5,948,410.
[38] WO2007/052163.
[39] WO2008/068631.
[40] Rota et al. (1992) *J Gen Virol* 73:2737-42.
[41] GenBank sequence GI:325176.
[42] Holmes et al. (2005) *PLoS Biol.* 3(9):e300.
[43] McCullers et al. (1999) *J Virol* 73:7343-8.
[44] GenBank sequence GI:325237.
[45] Herlocher et al. (2004) *J Infect Dis* 190(9):1627-30.
[46] Le et al. (2005) *Nature* 437(7062):1108.
[47] Banzhoff (2000) *Immunology Letters* 71:91-96.
[48] Lasley (2007) *Pediatric Asthma, Allergy & Immunology.* 20(3): 201-5.
[49] Coop et al. (2008) *Int Arch Allergy Immunol.* 146(1): 85-8.
[50] WO2009/001217
[51] Treanor et al. (1996) *J Infect Dis* 173:1467-70.
[52] Keitel et al. (1996) *Clin Diagn Lab Immunol* 3:507-10.
[53] U.S. Pat. No. 4,680,338.
[54] U.S. Pat. No. 4,988,815.
[55] WO92/15582.
[56] Johnson et al. (1999) *Bioorg Med Chem Lett* 9:2273-2278.
[57] Evans et al. (2003) *Expert Rev Vaccines* 2:219-229.
[58] WO03/011223.
[59] Wong et al. (2003) *J Clin Pharmacol* 43(7):735-42.
[60] US2005/0215517.
[61] Potter & Oxford (1979) *BrMed Bull* 35: 69-75.
[62] WO90/14837.
[63] Podda & Del Giudice (2003) *Expert Rev Vaccines* 2:197-203.
[64] Podda (2001) *Vaccine* 19: 2673-2680.
[65] *Vaccine Design: The Subunit and Adjuvant Approach* (eds. Powell & Newman) Plenum Press 1995 (ISBN 0-306-44867-X).
[66] *Vaccine Adjuvants: Preparation Methods and Research Protocols* (Volume 42 of *Methods in Molecular Medicine* series). ISBN: 1-59259-083-7. Ed. O'Hagan.
[67] Allison & Byars (1992) *Res Immunol* 143:519-25.
[68] Hariharan et al. (1995) *Cancer Res* 55:3486-9.
[69] US-2007/014805.
[70] US-2007/0191314.
[71] WO95/11700.
[72] U.S. Pat. No. 6,080,725.
[73] WO2006/113373.
[74] WO2005/097181.
[75] Han et al. (2005) *Impact of Vitamin E on Immune Function and Infectious Diseases in the Aged at Nutrition, Immune functions and Health* EuroConference, Paris, 9-10 Jun. 2005.
[76] U.S. Pat. No. 6,630,161.
[77] WO2007/052155.
[78] WO2008/128939.
[79] WO2005/089837.
[80] U.S. Pat. No. 6,692,468.
[81] WO00/07647.
[82] WO99/17820.
[83] U.S. Pat. No. 5,971,953.
[84] U.S. Pat. No. 4,060,082.
[85] EP-A-0520618.
[86] WO98/01174.
[87] Bang & Robins (2005) *Biometrics* 61:962-72.
[88] Stürmer et al. (2006) *J Clin Epidemiol.* 59(5):437-47.
[89] Nichol et al. (2007) *NEJM* 357 (14): 1373-81.
[90] Nichol (2009) *Vaccine* 27(45):6305-11.
[91] Simonsen et al. (2005) *Arch Intern Med* 165:265-72.
[92] Simonsen et al. (2007) *Lancet Infect Dis* 7(10):658-66.

[93] Hak et al. (2002) *J Epidemiol Community Health* 56:951-5.
[94] Hak et al. (2006) *Int J Epidemiol* 35:800-2.
[95] Jackson et al. (2006) IJE 35:337-344.
[96] Groenwold et al. (2008) IJE 37:1422-29.
[97] Mannino et al. (2011) poster entitled "Effectiveness of MF59®-adjuvanted vs. non-adjuvanted seasonal influenza vaccines on hospitalizations of the elderly due to all respiratory illnesses", Fourth ESWI Influenza Conference.

TABLE 1

| | | Entire Cohort | | | | | |
|---|---|---|---|---|---|---|---|
| | | Fluad ™ | | Agrippal ™ | | Overall | |
| LHA | Provider | N | % | N | % | N | % |
| Bergamo | GP | 12,160 | 7.1 | 15,924 | 9.3 | 28,084 | 16.4 |
| Cremona | District | 21,745 | 12.7 | 20,903 | 12.2 | 42,648 | 24.9 |
| | GP | 14,507 | 8.5 | 14,170 | 8.3 | 28,677 | 16.8 |
| Lecco | District | 4,459 | 2.6 | 4,308 | 2.5 | 8,767 | 5.1 |
| | GP | 16,422 | 9.6 | 8,784 | 5.1 | 25,206 | 14.7 |
| Mantova | District | 7,413 | 4.3 | 7,370 | 4.3 | 14,783 | 8.6 |
| Pavia | District | 11,743 | 6.9 | 11,080 | 6.5 | 22,823 | 13.3 |
| Overall | | 88,449 | 51.7 | 82,539 | 48.3 | 170,988 | 100.0 |

TABLE 2

| Characteristic (at enrolment) | Fluad ™ (%) | Agrippal ™ (%) |
|---|---|---|
| Sex (% female) | 56.8 | 56.8 |
| Influenza vaccine last year (yes) | 94.9 | 94.1 |
| Smoke (current/former/never) | 6.8/25.9/67.3 | 7.5/25.5/67.0 |
| Functional limitation daily activities (severe/mild/no) | 16.9/30.5/52.6 | 12.3/27.1/60.6 |
| Functional limitation climbing stairs (severe/mild/no) | 17.3/32.8/49.9 | 12.8/29.6/57.6 |
| Sharing house environment with children (always/sometimes/no) | 14.4/21.6/64.0 | 15.3/22.2/62.5 |
| Recent flu symptoms | 0.6 | 0.7 |
| Recent infectious disease | 0.2 | 0.2 |
| Recent transfusion | 0.3 | 0.3 |
| Recent intestine disorder | 0.9 | 1.0 |
| COPD | 11.9 | 10.4 |
| History of pneumonia, influenza or emphysema | 3.0 | 2.3 |
| Chronic Kidney Disease | 0.9 | 0.7 |
| Cancer | 15.1 | 14.2 |
| Diabetes | 15.9 | 15.0 |
| Heart disease | 75.1 | 72.1 |
| Vascular disease | 7.2 | 6.1 |
| Age (mean years) | 76.5 | 74.9 |

TABLE 3

| | | Fluad | | Agrippal | |
|---|---|---|---|---|---|
| LHA - Provider | Age (years) | Person-seasons | Cases | Person-seasons | Cases |
| Bergamo - GP | 65-69 | 1,464 | 1 | 1,908 | 2 |
| | 70-74 | 2,938 | 3 | 4,070 | 2 |
| | 75-79 | 2,833 | 2 | 3,729 | 8 |
| | 80-84 | 2,024 | 8 | 2,433 | 6 |
| | 85+ | 1,510 | 7 | 1,565 | 10 |
| Cremona - District | 65-69 | 4,853 | 3 | 4,772 | 2 |
| | 70-74 | 6,135 | 4 | 5,959 | 10 |
| | 75-79 | 5,457 | 5 | 5,352 | 6 |
| | 80-84 | 3,579 | 4 | 4,353 | 1 |
| | 85+ | 1,683 | 5 | 1,429 | 0 |
| Cremona - GP | 65-69 | 2,728 | 1 | 2,971 | 2 |
| | 70-74 | 3,277 | 1 | 3,351 | 5 |
| | 75-79 | 3,346 | 3 | 3,249 | 1 |
| | 80-84 | 2,881 | 6 | 2,665 | 6 |
| | 85+ | 2,214 | 6 | 1,884 | 10 |
| Lecco - District | 65-69 | 1,190 | 0 | 1,280 | 2 |
| | 70-74 | 1,322 | 1 | 1,414 | 1 |
| | 75-79 | 1,066 | 0 | 975 | 1 |
| | 80-84 | 628 | 1 | 460 | 2 |
| | 85+ | 248 | 1 | 172 | 1 |
| Lecco - GP | 65-69 | 1,949 | 4 | 1,467 | 0 |
| | 70-74 | 2,795 | 7 | 1,743 | 2 |
| | 75-79 | 3,471 | 4 | 1,866 | 4 |
| | 80-84 | 3,580 | 10 | 1,776 | 7 |
| | 85+ | 2,282 | 9 | 1,165 | 5 |
| Mantova - District | 65-69 | 1,346 | 1 | 1,886 | 1 |
| | 70-74 | 2,072 | 0 | 2,494 | 7 |
| | 75-79 | 1,928 | 1 | 1,579 | 1 |
| | 80-84 | 1,383 | 3 | 913 | 2 |
| | 85+ | 670 | 2 | 487 | 2 |
| Pavia - District | 65-69 | 1,380 | 0 | 3,984 | 0 |
| | 70-74 | 2,452 | 2 | 4,228 | 1 |
| | 75-79 | 3,851 | 5 | 1,793 | 1 |
| | 80-84 | 2,650 | 3 | 724 | 1 |
| | 85+ | 1,379 | 2 | 347 | 0 |
| Total | | 84,564 | 115 | 79,443 | 112 |

TABLE 4

| | | OR | 95% Confidence Limits | |
|---|---|---|---|---|
| Vaccine | Fluad vs Agrippal | 0.77 | 0.59 | 0.99 |
| PS quintile | 1 | 1.00 | | |
| | 2 | 2.35 | 1.11 | 4.99 |
| | 3 | 3.00 | 1.34 | 6.73 |
| | 4 | 1.98 | 0.82 | 4.83 |
| | 5 | 2.20 | 0.72 | 6.70 |
| Age | 1 year | 1.07 | 1.04 | 1.11 |
| Sex | Male vs Female | 2.24 | 1.67 | 3.00 |
| Season | 1 | 1.00 | | |
| | 2 | 1.13 | 0.74 | 1.73 |
| | 3 | 1.89 | 1.26 | 2.83 |
| LHA - Provider | Cremona district | 1.00 | | |
| | Bergamo GP | 1.20 | 0.63 | 2.32 |
| | Cremona GP | 1.10 | 0.70 | 1.72 |
| | Lecco district | 1.42 | 0.71 | 2.83 |
| | Lecco GP | 1.94 | 1.15 | 3.26 |
| | Mantova district | 1.32 | 0.76 | 2.30 |
| | Pavia district | 0.72 | 0.40 | 1.31 |
| Physical impairment | 1 grade | 0.80 | 0.71 | 0.90 |
| Recent intestine disorder | | 2.00 | 0.86 | 4.64 |
| History of lung hospitalization | | 3.39 | 2.26 | 5.08 |
| COPD | | 2.55 | 1.88 | 3.46 |
| History of vascular disease | | 1.25 | 0.83 | 1.89 |
| History of chronic kidney disease | | 2.91 | 1.48 | 5.73 |

TABLE 5

| Risk window | OR * | 95% Confidence Limits | |
|---|---|---|---|
| Broad | 0.91 | 0.78 | 1.05 |
| Intermediate | 0.85 | 0.69 | 1.05 |
| Narrow | 0.77 | 0.59 | 0.99 |

* Adjusted

The invention claimed is:
1. A method for reducing an elderly subject's incidence of hospitalization for influenza respiratory illness, comprising administering at least a priming, first dose of a tetravalent influenza vaccine adjuvanted with a squalene-containing oil-in-water emulsion to the elderly subject in consecutive influenza seasons, whereby the elderly subject's incidence of hospitalization for influenza respiratory illness is reduced relative to an elderly subject who receives an unadjuvanted influenza vaccine, wherein the elderly subject who receives the adjuvanted tetravalent influenza vaccine is receiving immunosuppressive therapy and ranges from 65-100 years old; further wherein the recipient of the adjuvanted influenza vaccine does not receive an unadjuvanted influenza vaccine during any of the consecutive influenza seasons.

2. The method of claim 1, wherein the emulsion comprises squalene, α tocopherol, and polysorbate 80.

3. The method of claim 1, wherein the emulsion has submicron oil droplets with an average diameter ranging from 100 to 250 nm.

4. The method of claim 1, wherein the adjuvanted tetravalent influenza vaccine is a split virus antigen vaccine.

5. The method of claim 1, wherein the adjuvanted tetravalent influenza vaccine is a purified surface antigen vaccine.

6. The method of claim 1, wherein the emulsion has droplets with a size less than 220 nm.

7. The method of claim 1, wherein at least 90% of the droplets (by volume) in the emulsion have a size less than 200 nm.

8. The method of claim 1, wherein the adjuvanted tetravalent influenza vaccine is administered intramuscularly.

9. The method of claim 1, wherein the elderly subject is a community-dwelling elderly subject.

10. The method of claim 1, wherein the adjuvanted and unadjuvanted vaccines have the same dosage volume, amount of antigen, virus strains, antigen type, and non-adjuvant excipients.

11. The method of claim 10, wherein the adjuvanted vaccine comprises the unadjuvanted vaccine and an adjuvant.

12. A method for reducing an elderly subject's incidence of hospitalization for influenza respiratory illness, comprising administering at least a priming, first dose of a tetravalent influenza vaccine adjuvanted with a squalene-containing oil-in-water emulsion to the elderly subject in consecutive influenza seasons, whereby the elderly subject's incidence of hospitalization for influenza respiratory illness is reduced relative to an elderly subject who receives an unadjuvanted influenza vaccine, wherein the elderly subject who receives the adjuvanted tetravalent influenza vaccine is receiving immunosuppressive therapy and ranges from 65-100 years old, and wherein the concentration of squalene in the oil-in-water emulsion ranges from 2 to 10% by weight; further wherein the recipient of the adjuvanted influenza vaccine does not receive an unadjuvanted influenza vaccine during any of the consecutive influenza seasons.

13. The method of claim 12, wherein the concentration of squalene in the oil-in-water emulsion ranges from 4.3 to 5% by weight.

14. The method of claim 12, wherein the adjuvanted tetravalent influenza vaccine is a split virus antigen or purified surface antigen vaccine.

15. The method of claim 12, wherein the adjuvanted tetravalent influenza vaccine is administered intramuscularly.

16. The method of claim 12, wherein the adjuvanted and unadjuvanted vaccines have the same dosage volume, amount of antigen, virus strains, antigen type, and non-adjuvant excipients.

17. The method of claim 16, wherein the adjuvanted vaccine comprises the unadjuvanted vaccine and an adjuvant.

18. The method of claim 1, wherein the adjuvanted tetravalent influenza vaccine is not administered as a second, booster dose.

19. The method of claim 1, further comprising administering a second, booster dose of the adjuvanted tetravalent influenza vaccine.

20. The method of claim 12, wherein the adjuvanted tetravalent influenza vaccine is not administered as a second, booster dose.

21. The method of claim 12, further comprising administering a second, booster dose of the adjuvanted tetravalent influenza vaccine.

* * * * *